US006204403B1

(12) United States Patent
Pepe et al.

(10) Patent No.: US 6,204,403 B1
(45) Date of Patent: Mar. 20, 2001

(54) PROCESS FOR MANUFACTURING ACRYLAMIDOALKYLALKOXYSILANES

(75) Inventors: Enrico J. Pepe, Winterhaven, FL (US); Anne Kathryn McMullen, Marietta; Scot M. Turner, Newport, both of OH (US); Keith J. Weller, Yonkers, NY (US)

(73) Assignee: Crompton Corporation, Greenwich, CT (US)

( * ) Notice: Subject to any disclaimer, the term of this patent is extended or adjusted under 35 U.S.C. 154(b) by 0 days.

(21) Appl. No.: 09/333,191

(22) Filed: Jun. 14, 1999

(51) Int. Cl.$^7$ .......................................................... C07F 7/10
(52) U.S. Cl. ...................................... 556/419; 252/183.12
(58) Field of Search ........................ 556/419; 252/183.12

(56) References Cited

U.S. PATENT DOCUMENTS

| 4,209,455 | * | 6/1980 | Pepe ...................................... 556/419 |
| 4,874,822 | * | 10/1989 | Rasmussen et al. .................. 525/279 |
| 5,550,272 | * | 8/1996 | Lewis et al. .......................... 556/479 |

* cited by examiner

*Primary Examiner*—Paul F. Shaver
(74) *Attorney, Agent, or Firm*—Shirley S. Ma

(57) ABSTRACT

A method for preparing acrylamidoalkylalkoxysilanes from aminoalkylalkoxysilanes and acrylate esters is described wherein at least two inhibitors and an amidation catalyst are used in an elevated temperature reaction.

18 Claims, No Drawings

PROCESS FOR MANUFACTURING ACRYLAMIDOALKYLALKOXYSILANES

FIELD OF THE INVENTION

This invention relates to an improved process for the production of acrylamidoalkylalkoxysilanes which find use as coupling agents.

BACKGROUND OF THE INVENTION

Certain methacrylate-functional silanes have been known, including, for example, 3-methacryloxypropyltrimethoxysilane, which has uses in glass fiber-reinforced composites of various thermoplastics and in durable coatings for metallic substrates. There has been a continuing need for products with differentiated and improved performance in areas in which 3-methacryloxypropyltrimethoxysilane is used, whereby differences in molecular structure result in useful differences in silane performance in properties as diverse as rate of hydrolysis, aqueous solubility, low product color, process-ability of the substrate being treated from aspects of lubricity, static control, fiber strength, speed of fiber drawing, and the like. One class of structural variations which has become useful relative to 3-methacryloxypropyltrimethoxysilane is the class of methacrylamidoalkylalkoxysilanes. Prior to the present invention, the processes for the production of acrylamidoalkylalkoxysilanes have had at least one major deficiency.

One early disclosure for the preparation of acrylamidoalkylalkoxysilanes is U.S. Pat. No. 3,249,461, wherein aminopropyltrimethoxysilane is reacted with methacryloyl or acryloyl chloride in an inert solvent blend. The reaction generates an equimolar amount of hydrogen chloride by-product, which was removed by washing the product/by-product mixture with excess aqueous sodium carbonate. Deficiencies of this process include the use of solvents, which lowers yield based on unit volume of production equipment, the formation of hydrogen chloride by-product necessitating its removal, and the removal of hydrogen chloride by aqueous washing, which will hydrolyze a significant portion of the methoxysilane groups forming higher oligomeric or polymeric siloxanes.

The above process has been modified in U.S. Pat. No. 4,711,943 wherein the hydrogen chloride by-product has been handled by formation of tertiary amine hydrochloride salt, which can be removed by filtration or centrifugation. Solvent is still used, and the formation and removal of solid tertiary amine hydrochloride salts further reduces yield per unit volume, adds a difficult and time-consuming step, and generates an undesirable waste which must be disposed of or treated for recycle. U.S. Pat. No. 3,249,461 also discloses that the corresponding acid anhydride may be used in place of the acid chloride, and U.S. Pat. No. 3,900,679 discloses formation of methacrylamidoalkylalkoxysilanes by reaction of aminoalkylsilanes with methacrylic acid. Reaction of amines with acids, which would also be by-products of the acid anhydride route above, to form amide groups is accompanied by the formation of an equimolar amount of water. As is known in the art, water will hydrolyze two equivalent amounts of the alkoxysilane groups, forming siloxanes, which reduce product purity, and build molecular weight and viscosity, potentially to the point of gelation.

U.S. Pat. No. 4,990,641 teaches a hydrosilation route to structurally different methacrylamidoalkyl-bis-alkoxysilanes as well as an acid chloride route to similar structures. The hydrosilation route to methacrylamidoalkylalkoxysilanes may be complicated by cyclizations of the N-allyl(meth)acrylamide starting materials under reaction conditions (Chem. Abstr., 95, 94175r(1976)). Lastly, the reaction of silazacyclobutanes with acid chlorides is disclosed in U.S. Pat. No. 5,446,180 and the reaction of acid chlorides with silazacyclopentanes in U.S. Pat. No. 5,082,958. This approach is practical only for monofunctional alkoxysilanes, which are of less utility than the di- and trialkoxysilane derivatives. It also requires the intermediate preparation of the commercially unavailable silazacycloalkanes. Thus, while utility for methacrylamidoalkylalkoxysilanes has been increasing (see U.S. Pat. Nos. 4,243,426, 4,762,759, 5,008,349, and 5,372,841 among others), there is still a need for improved processes to make said methacrylamidoalkylalkoxysilanes.

While the reaction of aminoalkylsilanes with acrylate esters is known as disclosed in U.S. Pat. No. 4,209,455, which is incorporated herein by reference, the reaction conditions are such that Michael addition of the amine group to the acrylate double bond is the first reaction which occurs, and the products are devoid of (meth)acrylate functionality.

SUMMARY OF THE INVENTION

Acrylamidoalkylalkoxysilanes are prepared by reactions of aminoalkylalkoxysilanes containing at least one —NH— group and at least one alkoxy group on silicon with acrylate esters, in the presence of an effective amount of an amidation catalyst and an effective amount of an inhibitor system at an elevated reaction temperature. The reactions preferably are run in the absence of added solvents, including tertiary amines or water washes used in prior art processes to remove acid by-products.

DETAILED DESCRIPTION OF THE INVENTION

It is an objective of this invention to provide a process for the production of acrylamidoalkylalkoxysilanes which provides high yields per unit volume of production equipment, i.e., the majority of the occupied reactor volume is filled with product, and not with solvents, by-products, or water washes. Preferably, greater than 60% of the occupied volume in the reactor will be filled with product prior to and during purification, more preferably greater than 75%, and most preferably greater than 90%, i.e., preferably there is less than 25% by volume of solvent, and most preferably less than 10% by weight solvent. While the process of this invention does not require the use of solvents, solvents may be used to a limited extent if needed to control temperature or viscosity.

The process of this invention does not require the use of tertiary amines or aqueous washes to remove acid by-products. Preferably, the process is run under essentially anhydrous conditions, i.e., there is less than 0.1 wt % water throughout the entire process, and more preferably less than 0.01 wt % water.

It is a further objective of this invention to provide processes yielding acrylamidoalkylalkoxysilanes with high shelf stability toward acrylate polymerization, preferably at least three months, more preferably six months, and most preferably, at least one year, and high process reproducibility, including avoidance of polymerization during the preparation and purification steps. It is another objective of this invention to provide purified acrylamidoalkylalkoxysilanes, having low color, i.e., less than 100 on the platinum/cobalt scale as described in ASTM Method D-1209, so that said silanes do not contribute undesired color to the products in which they are used. It is a further objective of this invention to provide processes for the production of acrylamidoalkylalkoxysilanes, which employ readily available raw materials, intermediates, and production equipment and which allow for easy purification of the silanes to high purities, i.e., greater than 95%, by standard means, as by simple distillation.

The process of the present invention involves the reaction of an aminoalkylalkoxysilane, containing at least one primary or secondary amine group with an acrylate ester in the presence of an effective amount of an amidation catalyst and an effective amount of an inhibitor system at a relatively high reaction temperature. For the purposes of the present invention an acrylate ester includes, but is not limited to, methacrylate esters, or esters which have alkyl substituents on the unsaturated carbons which are alpha and/or beta to the carboxylate.

The process is represented by the reaction shown:

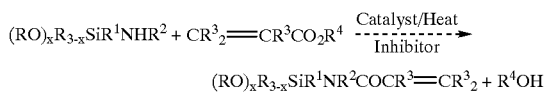

$$(RO)_xR_{3-x}SiR^1NHR^2 + CR^3{}_2{=}CR^3CO_2R^4 \xrightarrow[\text{Inhibitor}]{\text{Catalyst/Heat}}$$

$$(RO)_xR_{3-x}SiR^1NR^2COCR^3{=}CR^3{}_2 + R^4OH$$

where each R is a lower alkyl group of one to ten carbon atoms, $R^1$ is a linear, branched, cyclic, or substituted divalent hydrocarbon radical of one to twelve carbon atoms which may include heteroatoms, $R^2$ is hydrogen, R, or a monovalent aromatic hydrocarbon radical of six to twelve carbon atoms, an aminoalkyl group or a silyl functionality, and x is 1, 2, or 3, $R^3$ is H, R, a monovalent aromatic hydrocarbon radical of six to twelve carbon atoms or any two $R^3$'s are hydrocarbons, they may be connected to form a ring structure in the molecule, and $R^4$ is R or a monovalent aromatic hydrocarbon radical of six to twelve carbon atoms. Each R, $R^1$ and $R^3$ may be the same or different from each other so long as at least one of the three $R^3$'s in the acrylate ester is other than hydrogen.

R preferably is an alkyl group of one to four carbon atoms. More preferably, R is an alkyl group of one or two carbon atoms, i.e., methyl or ethyl. Preferably, $R^1$ has one to six carbon atoms. The aminoalkyl group of $R^2$ may be of the formula $-(CH_2)_nNHR^2$ where n is 2 to 4. The silyl group of $R^2$ may be of the formula $-R^1SiR_{3-x}(OR)_x$. $R^3$ preferably is hydrogen or an alkyl. Examples of R are ethyl, methyl, isopropyl or t-butyl. Examples of $R^1$ are $-(CH_2)_3-$, $-CH_2-CH(CH_3)-CH_2-$, $-(CH_2)_2O(CH_2)_2-$, $-(CH_2)_2C_6H_4(CH_2)_2-$, and $-(CH_2)_2$cyclo-$C_6H_{10}$-$(CH_2)_2-$. Examples of $R^2$ are H, $-CH_3$, $-CH_2CH_3$, $-C_6H_5$, $-C_2H_4NH_2$, $-C_2H_4NHCH_2CH_3$, $-C_2H_4NHC_6H_5$, $-CH_2C(CH_3)_3$, $-C_3H_6Si(OCH_3)_2CH_3$, and $-CH(CH_3)_2$. Examples of $R^3$ and $R^4$ are $-CH_3$, $-CH_2CH_3$, $-C_6H_5$. Most preferably, $R^1$ is a 1,3-propylene group, and $R^2$ is hydrogen.

Preferred starting silanes are selected from the group of aminoalkylalkoxysilanes, including aminopropyltrimethoxysilane, aminopropyltriethoxysilane, aminopropylmethyldimethoxysilane, aminopropylmethyldiethoxysilane, aminobutyltrimethoxysilane, aminobutyltriethoxysilane, aminobutylmethyldimethoxysilane, aminobutylmethyldiethoxysilane, aminoethylaminopropyltrimethoxysilane, aminoethylaminopropyltriethoxysilane, aminoethylaminopropylmethyldimethoxysilane, aminoethylaminopropylmethyldiethoxysilane, N-methylaminopropyltrimethoxysilane, aminopropyldimethylmethoxysilane, bis-(γ-trimethoxysilylpropyl)amine and other aminoalkylalkoxysilanes capable of forming amides on reaction with methacrylate esters. Most preferably, the aminoalkylalkoxysilanes are aminopropyltrimethoxysilane or aminopropyltriethoxysilane.

The methacrylate ester may be selected from the group of methyl methacrylate, ethyl methacrylate, propyl methacrylate, methyl crotonate, ethyl crotonate, $(CH_3)_2C{=}CHCO_2CH_3$, $CH_3CH{=}C(CH_3)CO_2CH_3$, and the like, recognizing that the alcohol released on amide formation will undergo exchange with the alkoxy groups on silicon, forming a mixture of products. It is preferable that methyl or ethyl methacrylate be used. It is not necessary that the acrylate ester and the aminoalkylalkoxysilane contain the same alkoxy group. For example, aminopropyltriethoxysilane will react with methyl methacrylate to provide a methacrylamidopropylalkoxysilane containing all possible combinations of ethoxy and methoxy groups on silicon, due to the formation of methanol as the alcohol by-product and its displacement of ethanol from silicon under reaction conditions. It should be noted correspondingly that reactions of aminopropyltrimethoxysilane with methyl methacrylate and of aminopropyltriethoxysilane with ethyl methacrylate will yield the respective single products with only ethoxy or methoxy groups on silicon.

In general, a stoichiometric excess of the acrylate ester is preferred, to maximize conversion of the aminoalkylalkoxysilane to acrylamidoalkylalkoxysilane. The molar ratio of acrylate ester to aminoalkylalkoxysilane may be in the range of 1.01 to 2.0 or higher, with 1.1 to 1.7 being preferred, and 1.25 to 1.45 being most preferred.

The amidation catalyst is a catalyst capable of forming amides from acrylate esters and aminoalkylalkoxysilanes, typically a Lewis acid and preferably a metal-containing Lewis acid selected from compounds of tin, titanium, aluminum, cobalt, zinc, iron, or lead, more preferably a compound of tin selected from the groups of dibutyltin dilaurate, stannous octoate, and dibutyl tin oxide, and most preferably dibutyltin oxide, used at a level of 0.05 to 2.0 wt-% relative to aminoalkylalkoxysilane, more preferably 0.1 to 1.0 wt-%, and most preferably 0.5 wt-%.

The inhibitor package contains at least two, and preferably at least three different inhibitor components, one being a volatile inhibitor, i.e., having a boiling point in the range of 60–150° C., more preferably 80–130° C., and most preferably 90–120° C. The volatile inhibitor is preferably a secondary amine, more preferably a dialkyl amine, and most preferably dipropylamine, which inhibitor is capable of codistilling with the acrylate ester and the alcohol by-product and preventing polymerization of the acrylate ester in upper areas of the reactor.

The second inhibitor component is a standard inhibitor with intermediate volatility which is capable of codistilling with the product or product mixture, i.e., has a boiling point in the range of 150–370° C., more preferably 200–300° C., and most preferably 225–275° C. The second inhibitor component is preferably not an aromatic amine or phenol which contains an aminomethylaryl grouping. While inhibitors containing aminomethylaryl groupings, e.g., 2,6-di-t-butyl-4-(dimethylamino)methylphenol, are known to be effective inhibitors for unsaturated silanes (see U.S. Pat. Nos. 5,103,032 and 5,145,979), their use is contraindicated in the present invention due to unexplained formation of undesired color. Accordingly, the second inhibitor preferably is selected from the groups of phenols, thiophenols, hindered cycloaliphatic amines, stable nitroxides, and aromatic amines with nitrogen directly bonded to an aromatic ring, including 2,6-di-t-butyl-4-methylphenol, p-methoxythiophenol, 2-t-butyl-4-methoxyphenol, p-methoxyhydroquinone, 2,2,6,6-tetramethylpiperidine, TEMPO (2,2,6,6-tetramethylpiperidinyloxy free radical) and 4-hydroxyTEMPO, diphenylamine, phenothiazine, and the like. Most preferably, the second inhibitor component in the inhibitor package is IONOL (Shell Chemical Co., Houston, Tex.) (2,6-di-t-butyl-4-methylphenol).

The optional third inhibitor component is a standard high boiling, nonvolatile inhibitor, not capable of codistilling with the product or product mixture and remains in the pot residue after distillation, allowing easy removal of same from the distillation unit. Selection from a wide variety of heavy inhibitors should suffice; preferred examples include higher molecular weight substituted phenols such as the styrenated phenols or octadecyl 3-(3,5-di-t-butyl-4-hydroxyphenyl)propionate, bisphenols such as 2,2'-methylenebis(6-t-butyl-p-cresol) or 4,4'-methylenebis(2,6-di-t-butylphenol), thiobisphenols such as SANTONOX (Flexsys America, Akron, Ohio) antioxidant 4,4'-thio-bis(6-t-butyl-m-cresol), 1,1'-thiobis(2-naphthol), or 2,2'-thiobis(4-methyl-6-t-butylphenol), polyphenol compounds such as IRGANOX 1010 (Ciba Specialty Chemicals, Tarrytown, N.Y.), tetrakis[methylene-3-(3,5-di-t-butyl-4-hydroxyphenyl)propionate]methane, or ETHANOX 330 (Ethyl Corp., Va.), 1,3,5-trimethyl-2,4,6-tris(3,5-di-t-butyl-4-hydroxybenzyl)benzene, and diarylamines such as N,N'-diphenyl-1,4-phenylenediamine. The optional heavy inhibitor preferably also will not contain an aminomethylaryl grouping and the most preferred candidate is SANTONOX antioxidant. The most volatile inhibitor component, for example, a secondary amine inhibitor, may be present in the acrylate ester in the range of 0.5 to 5.0 wt-%, preferably 1.0 to 3.5 wt-%, and most preferably 1.5 to 2.5 wt-%. The second inhibitor component, for example, IONOL, may be present in the product or product mixture in the range of 50 to 5000 parts per million (ppm) by weight, more preferably 50 to 125 ppm, and most preferably 50 to 75 ppm. The optional heavy inhibitor may be present in the product or product mixture in the range of 100 to 2000 ppm, with 200 to 1000 ppm being preferred, and 250 to 600 ppm being most preferred. It should be recognized that each component may include more than one inhibitor, i.e., may be a mixture, and that acrylate esters as commercially supplied will contain at least one inhibitor, which may or may not be considered part of the inhibitor package of the present invention.

While different modes of combination of the reactants, catalyst, and inhibitor package may be used, a preferred approach is to combine the aminoalkylalkoxysilane, the amidation catalyst, and one or more less volatile or heavy inhibitor in the reactor, heat to the reaction temperature, and add the methacrylate ester containing the volatile amine inhibitor to the mixture in the reactor. This allows the achievement and maintenance of a relatively high reaction temperature in the reactor. The reaction temperature should be in the range of 100–200° C., preferably 150–200° C., and most preferably 165–170° C. At the reaction temperature, the acrylate ester, the volatile amine inhibitor, and the by-product alcohol will be refluxing in the reactor head space, allowing removal of most of the by-product alcohol by distillation/codistillation. Removal of the by-product alcohol with the volatile amine inhibitor and some of the acrylate ester is a preferred means of maintaining high reaction temperature.

The reactor may be any of a variety of commercially used reaction vessels, with means of addition of one or more reactants, agitation, heating and cooling, condensing of vapors, maintenance of inert atmosphere, and transfer of the product or product mixture from the reactor. Reactions are run under an inert atmosphere, preferably of nitrogen, which may contain a small percentage of oxygen, preferably 3% relative to nitrogen, to enhance performance of the inhibitor package. While there is no distinct need for operation under pressure, the reactions may be run under pressure to assist in maintaining the high reaction temperature. While there is also no distinct need to run reactions under vacuum, it is preferable to apply high vacuum if the product is to be distilled.

Depending on the application, the product may be used as the devolatilized, filtered crude material, particularly if the optional heavy inhibitor is not used. It is preferable to distill the product to remove catalyst residues and any oligomeric or polymeric species which may have formed, particularly where low color and high shelf stability is desired, and distillations may be performed in the reactor or in a separate distillation unit. Distillation preferably is done under vacuum, in the range of 120–160° C. at 0.05 to 5 mm Hg.

EXAMPLES

The following examples are intended only to illustrate the process of the present invention.

Example 1—A 1-liter, 3-necked flask was equipped with a thermometer, magnetic stirring bar, distillation head with water condenser, receiver and cold trap, heating mantle, nitrogen flow valves, and dropping funnel modified with glass tube extension for sub-surface liquid addition. Aminopropyltriethoxysilane (558.3 g, 2.5 moles) and dibutyltin oxide (2.8 g, 0.011 mole, 0.5 wt-%) were charged and the stirred suspension heated to 165–170° C. Over a period of 2 hr, methyl methacrylate (500.5 g, 5.0 moles) inhibited with 10.1 g (0.1 mole, 2 wt-%) of dipropylamine was added at a uniform rate below the surface. Distillate was constantly removed at a head temperature of 90–110° C. After completion of addition, the mixture was sparged with nitrogen, treated with Celite filter aid and filtered, to remove small amounts of methacrylate polymer, resulting in 655 g of clear, light amber liquid. A 250 g portion was vacuum distilled, providing 220 g of product at 126–135° C./0.07–0.3 mm Hg, calculating to an 84.8% yield based on aminopropyltriethoxysilane. GC Analysis of the distilled product showed three of the possible four mixed alkoxysilanes. This example demonstrated polymer formation during the preparation step, due to lack of intermediate and heavy inhibitors.

Example 2—Example 1 was repeated in a similarly fitted 12-liter flask, using 5019 g (22.6 moles) of aminopropyltriethoxysilane, 24.4 g (0.09 mole, 0.5 wt-%) of dibutyltin oxide, and 3125 g (31.2 moles) of methyl methacrylate inhibited with 64 g (0.63 mole) of dipropylamine. Addition time was 5 hr. Batch distillation provided 4923 g (80.9% yield) of product mixture at 145° C./1 mm Hg. Distillation was stopped before completion to prevent gel formation in the flask. This example demonstrated polymer formation during distillation due to lack of intermediate and heavy inhibitors.

Example 3—Example 1 was repeated on a large scale with 1720 parts of methyl methacrylate, 25.5 parts of dipropylamine, 11.3 parts of dibutyltin oxide and 2324 parts of aminopropyltriethoxysilane. In addition, 1 part of 2,6-di-t-butyl-4-(dimethylaminomethyl)phenol was added to each of the methacrylate feed container and the distillation receiver, and 2.5 parts of 2,6-di-t-butyl-4-methylphenol (IONOL) was added to the silane. Addition of methacrylate was completed in 7 hr and 45 min. Vacuum stripping provided 2861 parts of crude product, of which 2461 parts were vacuum distilled at 165° C./1.5–4 mm Hg. Yield was 1828 parts (76%). While the process steps were free of polymer, the product developed an undesirable dark red color on standing.

Example 4—Example 3 was repeated four times except that IONOL alone was used instead of 2,6-di-t-butyl-4-(dimethylaminomethyl)phenol in one run, and the silane was combined with 0.2 parts of IONOL and 1 part of SANTONOX, with one part of IONOL in the receiver only (no 2,6-di-t-butyl-4-(dimethylaminomethyl)phenol) in three runs. The distilled products were very consistent with total purities (combined 4 possible mixed alkoxysilanes) of 97.0–99.8%, color of 5–10 on platinum/cobalt scale (ASTM Method D-1209), and good storage stability regarding avoidance of both color and polymer formation. The distilled product was confirmed to be a mixture of methacrylamidopropyltrialkoxysilanes with all possible combinations of methoxy and ethoxy groups via analyses by gas chromatography/mass spectrometry, Fourier transfer infrared spectrometry, and nuclear magnetic resonance spectrometry. In particular, the essential absence of Michael addition by-products was confirmed.

Example 5—Into a 500 ml round-bottomed three-necked flask equipped with magnetic stir bar, short path distillation head, nitrogen inlet, thermometer, heating mantle, temperature controller, and addition funnel modified to allow subnatant addition was placed SILQUEST A-1170 (bis-(γ-trimethoxysilylpropyl)amine) (Witco Corp.) (140.4 grams, 0.572 moles) and dibutyltin oxide (0.64 grams, 0.0026 moles). The solution was heated to 170° C., and a solution of methylmethacrylate (114.5 grams, 1.14 moles) and di-n-propylamine (2.27 grams, 0.022 moles) was added over a period of 1.5 hours. A distillate was continuously removed at a head temperature of approximately 100° C. After addition was complete, the solution was sparged with nitrogen for 20 minutes at 170° C., and then for 12 hours as the solution was allowed to cool to room temperature. The crude material was analyzed by GC/MS and found to contain 6% of the amidation product bis-(γ-trimethoxysilylpropyl) methacrylamide, 88% A-1170 (bis-(γ-trimethoxysilylpropyl)amine), and the balance unidentified higher molecular weight species.

What is claimed is:

1. A method for preparing acrylamidoalkylalkoxysilanes comprising:

reacting an aminoalkylalkoxysilane of the formula (RO)$_x$R$_{3-x}$SiR$^1$NHR$^2$ with an acrylate ester of the formula CR$^3_2$=CR$^3$CO$_2$R$^4$ where each R is a lower alkyl group of one to ten carbon atoms, R$^1$ is a linear, branched, cyclic, or substituted divalent hydrocarbon radical of one to twelve carbon atoms which may include heteroatoms, R$^2$ is hydrogen, R, or a monovalent aromatic hydrocarbon radical of six to twelve carbon atoms, an aminoalkyl group or a silyl functionality, and x is 1, 2, or 3, R$^3$ is H, R or a monovalent aromatic hydrocarbon radical of six to twelve carbon atoms wherein any two of three R$^3$'s may form a ring, R$^4$ is R or a monovalent aromatic hydrocarbon radical of six to twelve carbon atoms, each R, R$^1$ and R$^3$ may be the same or different from each other so long as at least one of the three R$^3$'s in the acrylate ester is other than hydrogen, in the presence of an effective amount of an amidation catalyst and an effective amount of an inhibitor package at an elevated reaction temperature.

2. The method of claim 1 comprising combining the aminoalkylalkoxysilane, one or more components of said inhibitor package, and the amidation catalyst in a reaction vessel, heating same to the elevated reaction temperature of 100 to 200° C., and adding the acrylate ester containing the remaining component of the inhibitor package.

3. The method of claim 2 wherein the aminoalkylalkoxysilane is selected from the group consisting of primary aminoalkyltrialkoxysilanes and primary aminoalkylmethyldialkoxysilanes, the inhibitor package is comprised of at least one intermediate or low volatility having boiling points greater than 150° C. and a volatile inhibitor having a boiling point of 60–150° C., the amidation catalyst is a Lewis acid, the elevated temperature is greater than 100° C.

4. The method of claim 3 wherein the Lewis acid amidation catalyst is an organometallic compound of tin, titanium, aluminum, cobalt, zinc, iron or lead, the volatile inhibitor having a boiling point of 60–150° C. is a secondary amine, the intermediate or low volatility inhibitor is comprised of a hindered phenol having a boiling point in the range of 200–300° C. and a non-volatile inhibitor having a boiling point greater than 370° C., and the elevated temperature is in the range of 150–200° C.

5. The method of claim 3 wherein the aminoalkylalkoxysilane is aminopropyltriethoxysilane, the hindred phenol is 2,6-di-t-butyl-4-methylphenol and the non-volatile inhibitor is 4,4-thio-bis (6-t-butyl-m-cresol), the amidation catalyst is dibutyltin oxide, the acrylate ester is methyl methacrylate used at a molar ratio of 1.1 to 1.7 relative to aminoalkylalkoxysilane, the volatile inhibitor is dipropylamine, and the elevated temperature is 165–170° C.

6. The method of claim 5 wherein the hindered phenol is present in the range of 50 to 2000 parts per million by weight of the reaction mixture, the non-volatile inhibitor is present in the range of 100 to 2000 parts per million by weight of the reaction mixture, and the amidation catalyst is present in the range of 0.1 to 1.0 wt-% relative to the aminoalkylalkoxysilane.

7. The method of claim 1 further comprising purifying the reaction mixture by distillation and wherein the occupied volume of the reactor after reaction and before and during purification comprises at least 75% by volume of the acrylamidoalkylalkoxysilane product.

8. The product prepared by the method of claim 1 comprising acrylamidoalkylalkoxysilane and an effective amount of an inhibitor package including at least two inhibitors.

9. The product of claim 8 comprising combinations of ethoxy and methoxy groups for the alkoxy groups on the acrylamidoalkylalkoxysilane.

10. A composition comprising:

(a) an aminoalkoxysilane of the formula (RO)$_x$R$_{3-x}$SiR$^1$NHR$^2$;

(b) an acrylate ester of the formula CR$^3_2$=CR$^3$CO$_2$R$^4$;

(c) an inhibitor with a boiling point of greater than 150° C.;

(d) an inhibitor with a boiling point of 60° C. to 150° C.; and (e) an amidation catalyst;

where each R is a lower alkyl group of one to ten carbon atoms, R$^1$ is a linear, branched, cyclic, or substituted divalent hydrocarbon radical of one to twelve carbon atoms which may include heteroatoms, R$^2$ is hydrogen, R, or a monovalent aromatic hydrocarbon radical of six to twelve carbon atoms, an aminoalkyl group or a silyl functionality, and x is 1, 2, or 3, $R^3$ is H, R or a monovalent aromatic hydrocarbon radical of six to twelve carbon atoms, $R^4$ is R or a monovalent aromatic hydrocarbon radical of six to twelve carbon atoms, and each R, $R^1$ and $R^3$ may be the same or different from each other so long as at least one of the three $R^3$'s in the acrylate ester is other than hydrogen.

11. A composition according to claim 10 wherein the amidation catalyst is selected from the group consisting of an organometallic compound of tin, titanium, aluminum, cobalt, zinc, iron or lead.

12. A composition according to claim 11 wherein the acrylate ester is methyl methacrylate or ethyl methacrylate.

13. A composition according to claim 12 wherein the silane is selected from the group consisting of aminopropyltrimethoxysilane, aminopropyltriethoxysilane, aminopropylmethyldimethoxysilane, aminopropylmethyldiethoxysilane, aminobutyltrimethoxysilane, aminobutyltriethoxysilane, aminobutylmethyldimethoxysilane, aminobutylmethyldiethoxysilane, aminoethylaminopropyltrimethoxysilane, aminoethylaminopropyltriethoxysilane, aminoethylaminopropylmethyldimethoxysilane, aminoethylaminopropylmethyldiethoxysilane, N-methylaminopropyltrimethoxysilane, and aminopropyldimethylmethoxysilane.

14. A composition according to claim 13 wherein the inhibitor (d) is a dialkyl amine.

15. A composition according to claim 14 additionally comprising a third inhibitor with a boiling point of greater than 300° C.

16. A composition according to claim 15 wherein the catalyst is dibutyltin oxide.

17. A composition according to claim 16 wherein the inhibitor (c) is a hindered phenol.

18. A composition according to claim 17 wherein the ester is present at a molar ratio of 1.1 to 1.7 relative to aminoalkylalkoxysilane.

* * * * *